Figure 1:
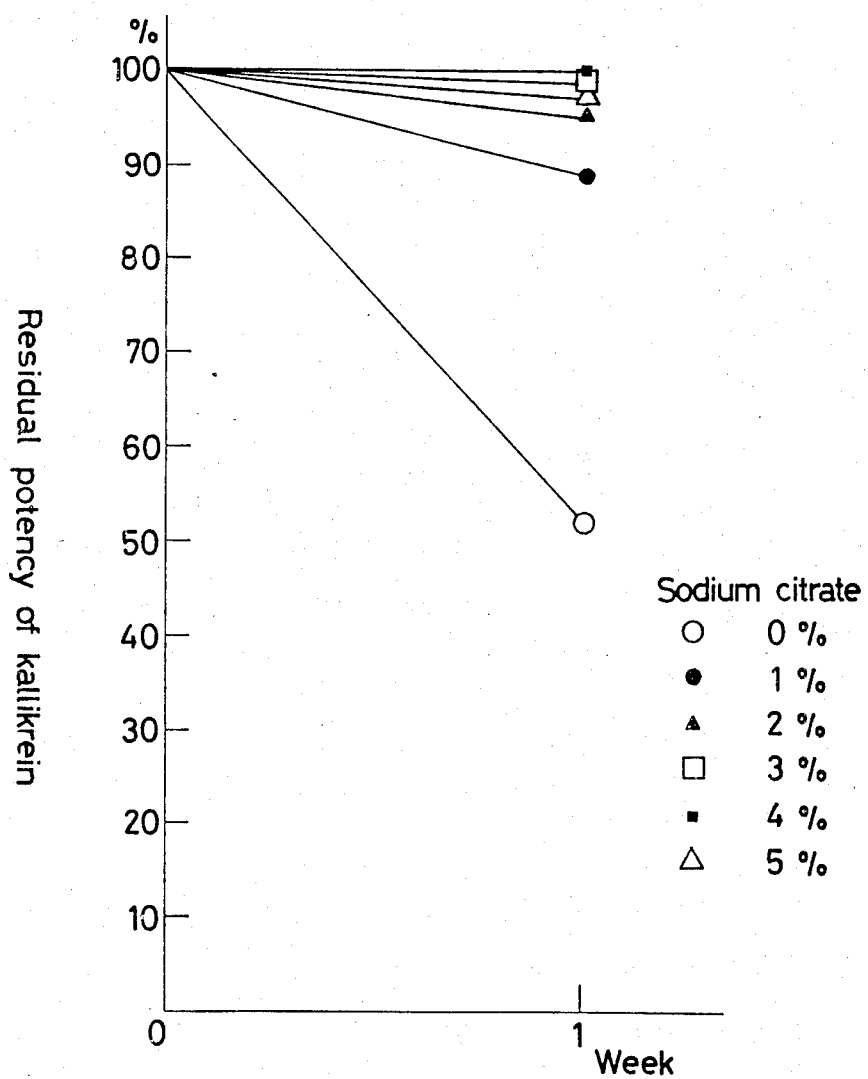

United States Patent [19]

Nakanishi et al.

[11] Patent Number: 4,500,514

[45] Date of Patent: Feb. 19, 1985

[54] PROCESS FOR PREPARING A HEAT-STABLE AQUEOUS SOLUTION OF HUMAN URINE KALLIKREIN AND PRODUCT PREPARED

[75] Inventors: Koichiro Nakanishi, Ashiya; Hajime Hiratani, Sennan, both of Japan

[73] Assignee: Japan Chemical Research Co., Ltd., Kobe, Japan

[21] Appl. No.: 557,107

[22] Filed: Dec. 1, 1983

[30] Foreign Application Priority Data

Dec. 2, 1982 [JP] Japan ................................ 57-212532

[51] Int. Cl.$^3$ .......................................... A61K 37/553
[52] U.S. Cl. ........................................ 424/94; 424/99
[58] Field of Search ..................................... 424/99, 94

[56] References Cited

PUBLICATIONS

Chemical Abstracts–10th Collect. Index, vol. 86–95 (1977–1981) pp. 29064cs–29068cs.

*Primary Examiner*—Sam Rosen
*Attorney, Agent, or Firm*—Burgess, Ryan & Wayne

[57] ABSTRACT

Human urine kallikrein dissolved in water is made heat-stable by the addition of a citric acid salt such as sodium citrate, so that an aqueous solution containing the kallikrein and the citric acid salt can be sterilized at 60° to 70° C.

9 Claims, 3 Drawing Figures

PROCESS FOR PREPARING A HEAT-STABLE AQUEOUS SOLUTION OF HUMAN URINE KALLIKREIN AND PRODUCT PREPARED

This invention relates to a process for preparing a heat-stable aqueous solution of human urine kallikrein and a process for treating the solution.

The object of this invention is to provide a heat-stable aqueous solution of human urine kallikrein and the preparation thereof.

Another object of this invention is to provide an aqueous solution of human urine kallikrein sterilized by heating.

Further object of this invention is to provide a process for inactivating microorganisms and/or viruses which may exist in the aqueous solution of human urine kallikrein without inactivating a substantial amount of the kallikrein.

Kallikrein is a kind of protease which is broadly distributed in the serum, urine and various organs, such as the pancreas, submandibular gland, kidney, etc., of mammalian animals. It acts on kininogens in plasma to release kallidin which is a polypeptide and this kallidin displays such physiological activities as smooth muscle contracting, antihypertensive and blood flow increasing activities. And swine pancreatic kallikrein has for some time been utilized as a drug for the treatment of hypertension, arteriosclerosis, angina pectoris, climacteric disturbance, etc. However, administration of such a drug derived from a heterologous animal protein to humans tends to cause immunological side effects.

Although human urine kallikrein is not being used as a drug today for the reason that its production cost is high because the material urine is not readily available and is lean in kallikrein, it is free from the antibody reaction which is encountered with swine kallikrein and, therefore, is excepted to be useful as an injectable drug free from side effects. Human urine kallikrein is not resistant to heat as are other glycoproteins and is inactivated at relatively low temperature under strongly acidic or strongly alkaline conditions. However, the present inventors demonstrated that it is comparatively resistant to heat under weekly acid to weekly basic conditions (Japanese Patent Application Nos. 119000/1982 and 113364/1982). The present inventors further conducted a research for developing an aqueous injection of human urine kallikrein and for finding a stabilizer for such injection. As shown in Table 1, among various compounds tested, sodium citrate showed a remarkably great stablizing effect and, thus, could be used as an effective thermal stabilizer for kallikrein.

TABLE 1

Screening of Stabilizers for Aqueous Solutions of Human Urine Kallikrein [To a 3 KU/ml solution of kallikrein in 0.9% NaCl—phosphate buffer (pH 7.0) was added a stabilizer and the mixture was stored at 70° C. for 7 days]

| Stabilizer | Level of addition (mg/ml) | Residual potency (%) | |
|---|---|---|---|
| Sodium benzoate | 50 | 57.7 | J.P. |
| Aminoacetic acid | 50 | 78.3 | " |
| L-Arginine.HCl | 20 | 69.9 | " |
| Benzalkonium chloride | 1 | 1.0 | " |
| Carboxymethylcellulose.Na | 50 | 92.3 | " |
| Sodium citrate | 50 | 101.8 | " |
| Glycerin | 50 | 52.0 | " |

TABLE 1-continued

Screening of Stabilizers for Aqueous Solutions of Human Urine Kallikrein [To a 3 KU/ml solution of kallikrein in 0.9% NaCl—phosphate buffer (pH 7.0) was added a stabilizer and the mixture was stored at 70° C. for 7 days]

| Stabilizer | Level of addition (mg/ml) | Residual potency (%) | |
|---|---|---|---|
| Gurcronic acid | 5 | 27.7 | Wako |
| Creatinine | 20 | 0.5 | " |
| Tartaric acid | 15 | 73.1 | J.P. |
| L-Cystein | 50 | 1.0 | Formulary of Food Additives |
| Gelatin | 5 | 75.0 | J.P. |
| D-Sorbitol | 50 | 5.2 | " |
| Sodium thioglycolate | 5 | 0.5 | Wako |
| Dextran (70) | 50 | 12.3 | J.P. |
| Nicotinamide | 50 | 64.6 | " |
| Methyl p-hydroxybenzoate | 50 | 53.6 | " |
| L-Histidine hydrochloride | 20 | 80.9 | Formulary of Food Additives |
| Propylene glycol | 50 | 61.2 | J.P. |
| Glucose | 50 | 1.6 | " |
| Phenol | 5 | 32.0 | " |
| Polyethylene glycol | 50 | 60.9 | S.C.R.M. |
| Mannitol | 50 | 61.6 | USP18 |
| Maleic acid | 4 | 64.0 | Wako |
| L-Methionine | 5 | 61.5 | J.P. |
| Glutamine | 5 | 70.3 | Wako |
| L-Serine | 10 | 64.1 | " |
| Bovine serum albumin | 5 | 75.9 | " |
| Control (no stabilizer) | | 55.3 | " |

(The abbreviation used in the table have the following meanings.)
J.P.: Japanese Pharmacopeia
F.A.: Formulary of Food Additives
S.C.R.M.: Standards of Cosmetic Raw Materials
USP: United States Pharmacopeia
Wako: Manufactured by Wako Pure Chemical Industries, Ltd.

Then, with sodium citrate as a candidate stabilizer, a detailed experimental study was conducted. Thus, as shown in the Examples that follow, the residual kallikrein activity in aqueous solutions of human urine kallikrein in the presence or absence of sodium citrate were investigated at the accelerated storage temperatures of 60°, 65° and 70° C. The study showed very interesting findings (See the Examples) which may be summarized below.

When an aqueous solution of human urine kallikrein was directly heated at 60° to 65° C., kallikrein activity in the solution dropped to 50 to 20% in about a week. However, when some amount of sodium citrate was added to the solution, more than 90% of the original kallikrein activity was retained under the same conditions. Thus, by adding sodium citrate to an aqueous injection of human urine kallikrein, it was possible to carry out heat-treatments such as virucide, pasteurization, etc. The above experiment can be considered to be an accelerated test on injections and the results suggest that the kallikrein injection can be stored at room temperature for a long time.

Based on the above findings, this invention is directed to a process for preparing a heat-stable aqueous solution of human urine kallikrein, which comprises contacting an effective amount of a pharmaceutically acceptable citric acid salt with human urine kallikrein in the form of aqueous solution.

The citric acid salt is a water-soluble salt and when said aqueous solution is intended for use as an injection, for instance, the salt is a pharmaceutically acceptable salt. As examples of such salt may be mentioned sodium citrate and potassium citrate. The salt may be used in the form of a neutral salt or an acidix salt, and it is optional to add citric acid in the form of such salt to the aqueous solution or add free citric acid to the aqueous solution and then neutralize the solution so that the acid will form such a salt in the solution.

The concentration of dissolved citric acid salt in the aqueous solution is preferably in the range of about 1 to 5%.

In addition to the citric acid salt, an osmotic pressure regulating agent such as sodium chloride may be added to the aqueous solution of human urine kallikrein if necessary.

The following examples are given to illustrate this invention in comparison with control (without addition of citric acid salt) for a better understanding of the invention.

Figure 2:
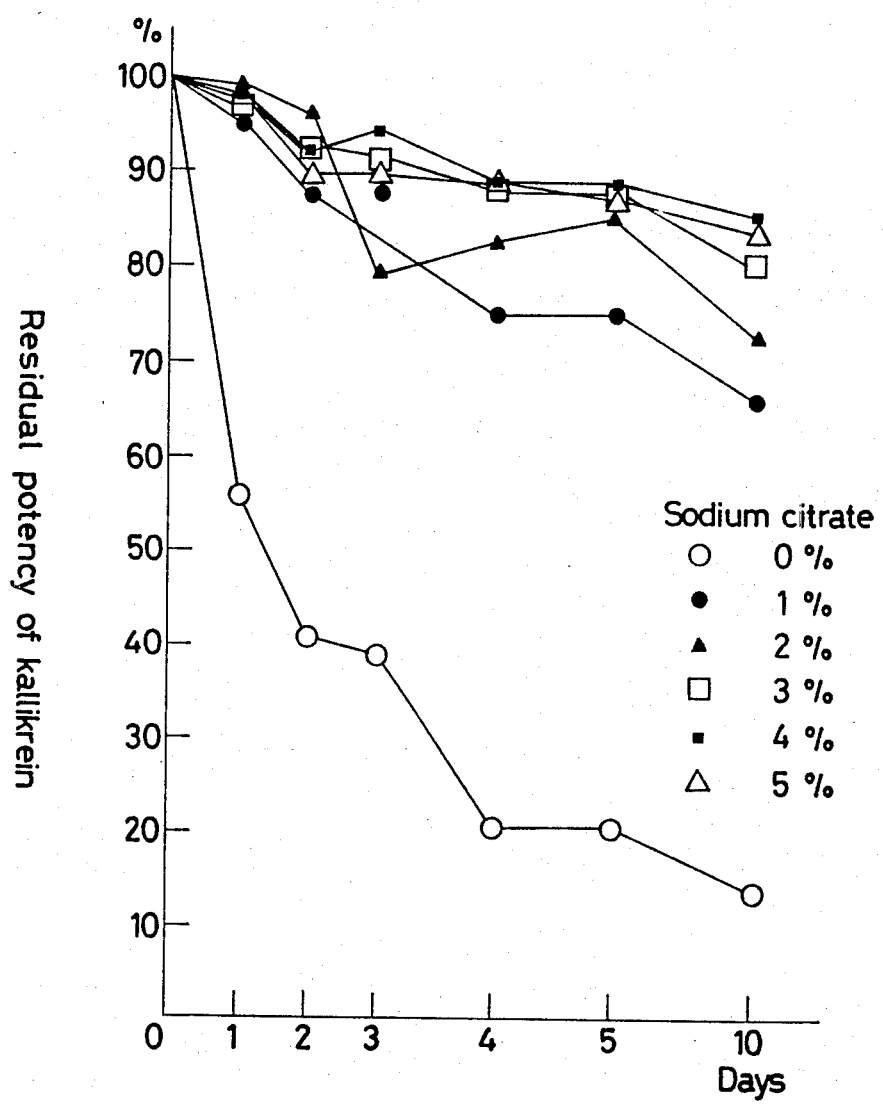
Figure 3:
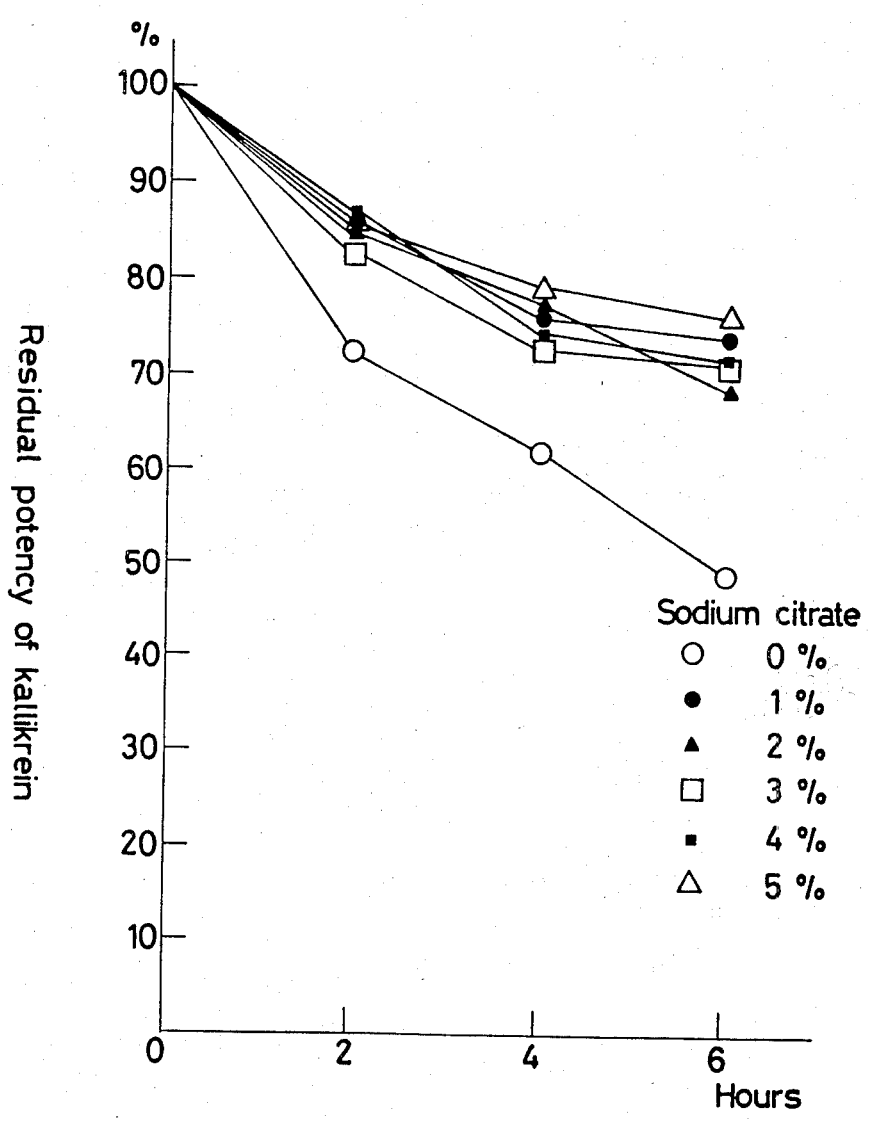

In the drawings, FIGS. 1, 2 and 3 are graphs showing the residual kallikrein activities in aqueous solutions of human urine kallikrein under the storage conditions of 60° C. and 1 week, 65° C. and 10 days, and 70° C. and 6 hours, respectively.

EXAMPLE 1

1. Materials (a) Sodium citrate ($Na_3C_6H_5O_7.2H_2O$) was dissolved in water to prepare 0, 1.2, 2.4, 3.6, 4.8 and 6.0% aqueous solutions. As the osmotic pressure ratios of the 0, 1.2 and 2.4% aqueous solutions of sodium citrate were less than 1.0, their ratios were adjusted to 1.0 by adding 0.68%, 0.37% and 0.09%, respectively, of sodium chloride. Sodium chloride was not added to the 3.6, 4.8 and 6.0% aqueous solutions, for their osmotic ratios were over 1.0.

(b) To 2.6 ml of an aqueous solution of human urine kallikrein (173.4 KU/ml) was added 12.4 ml of one of the sodium citrate solutions prepared in (a) above to give a solution containing 30 KU/ml of human urine kallikrein and 0 to 5% of sodium citrate. Each of such solutions was distributed in 0.5 ml portions into 1 ml-ampules which were then sealed to provide samples.

2. Test method

The experiment was performed at the following 4 different temperatures. The kallikrein activity of each sample was determined before and after the test and the residual activity rate was calculated with the activity before the test being taken as 100%.

3. Determination

The determination of kallikrein activity was carried out by the MCA substrate hydrolytic activity method (note) using proline-phenylalanine-arginine coumarinyl-methylamide as the substrate.

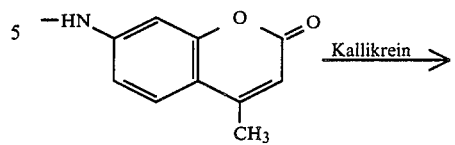

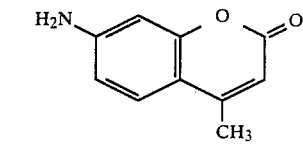

To 850 μl of 0.01 M-phosphate buffer (pH 7.4) was added 50 μl of a 0.1 M solution of the above substrate and the mixture was preincubated at 37° C. for 5 minutes. To this preincubated solution was added 100 μl of a 200-fold dilution of the sample and the mixture was incubated for 10 minutes. After cooling with ice, 20 μl of 10% acetic acid was added to the reaction mixture and using a spectrophotofluorometer (Shimadzu RF-510), the intensity of fluorescence at 460 nm was measured with an excitation wavelength of 380 nm. As a reference standard, 5 nM-aminomethylcoumarin was used as 100%.

4. Results

The heat stabilities of human urine kallikrein in the absence of sodium citrate and in the pressure of 1 to 5% of sodium citrate are shown in Tables 2 through 4 and FIGS. 1 through 3.

TABLE 2

| Heat Stability of Human Urine Kallikrein (60° C., 1 week) | | |
|---|---|---|
| Level of addition of sodium citrate, % | Day 0 | Day 7 |
| 0 | *666.06 | 347.01 |
|   |         | **52.1% |
| 1 | 694.62  | 618.81 |
|   |         | 89.1% |
| 2 | 666.06  | 633.42 |
|   |         | 95.1% |
| 3 | 608.94  | 596.76 |
|   |         | 98.0% |
| 4 | 627.30  | 615.75 |
|   |         | 98.2% |
| 5 | 636.48  | 617.06 |
|   |         | 96.9% |

*n moles of aminomethylcoumarin/min./ml (sample)
**Residual activity, with the value at hour-0 being taken as 100%. (The same applies hereinafter.)

TABLE 3

| Heat Stability of Human Urine Kallikrein (65° C., 10 days) | | | | | | | |
|---|---|---|---|---|---|---|---|
| Level of addition of sodium citrate (%) | Day 0 | Day 1 | Day 2 | Day 3 | Day 5 | Day 7 | Day 9 |
| 0 | *666.06 | 373.64 | 272.34 | 259.08 | 149.80 | 137.26 | 124.27 |
|   |         | **56.1% | 40.9% | 38.9% | 22.5% | 20.6% | 18.7% |
| 1 | 694.62 | 664.02 | 606.90 | 608.94 | 521.22 | 519.80 | 456.76 |
|   |        | 95.6% | 87.4% | 87.7% | 75.1% | 74.8% | 65.8% |
| 2 | 666.02 | 655.86 | 640.56 | 529.38 | 548.76 | 564.80 | 482.92 |
|   |        | 98.5% | 96.2% | 79.5% | 82.4% | 84.8% | 72.5% |
| 3 | 608.94 | 587.52 | 561.00 | 553.86 | 536.52 | 532.17 | 486.19 |
|   |        | 96.5% | 92.1% | 91.0% | 88.1% | 87.4% | 79.8% |
| 4 | 627.30 | 619.14 | 568.14 | 592.62 | 550.80 | 554.67 | 534.16 |
|   |        | 98.7% | 90.6% | 94.5% | 87.8% | 88.4% | 85.2% |

TABLE 3-continued

Heat Stability of Human Urine Kallikrein
(65° C., 10 days)

| Level of addition of sodium citrate (%) | Day 0 | Day 1 | Day 2 | Day 3 | Day 5 | Day 7 | Day 9 |
| --- | --- | --- | --- | --- | --- | --- | --- |
| 5 | 636.48 | 623.22 | 568.14 | 568.14 | 563.04 | 554.67 | 531.40 |
|   |        | 97.9%  | 89.3%  | 89.3%  | 88.5%  | 87.1%  | 83.5%  |

TABLE 4

Heat Stability of Human Urine Kallikrein
(70° C., 6 hours)

| Level of addition of sodium citrate (%) | Hour 0 | Hour 2 | Hour 4 | Hour 6 |
| --- | --- | --- | --- | --- |
| 0 | *566.10 | 411.06 | 347.82 | 277.44 |
|   |         | **72.6% | 61.4% | 49.0% |
| 1 | 593.64 | 503.88 | 449.82 | 438.60 |
|   |        | 84.9%  | 75.8%  | 73.9%  |
| 2 | 600.78 | 514.08 | 470.22 | 406.98 |
|   |        | 85.6%  | 78.3%  | 67.7%  |
| 3 | 600.78 | 497.76 | 434.52 | 425.34 |
|   |        | 82.9%  | 72.3%  | 70.8%  |
| 4 | 582.42 | 500.82 | 431.46 | 416.16 |
|   |        | 86.0%  | 74.1%  | 71.5%  |
| 5 | 609.96 | 522.24 | 481.44 | 459.00 |
|   |        | 85.6%  | 78.9%  | 75.3%  |

The above results lead to the following conclusions.

(1) Under the storage conditions of 60° C. and 1 week, kallikrein activity in the absence of sodium citrate decreased to nearly 50% of the initial level, whereas the residual activity was 90 to 98% when 1 to 5% of sodium citrate was added. Thus, under the above conditions, the addition of sodium citrate was quite effective.

(2) At the storage conditions of 65° C., residual kallikrein activity in the absence of sodium citrate was less than 60% after 1 day, 20% after 5 days, and close to 10% after 10 days. In the presence of 1 to 5% of sodium citrate, residual kallikrein activity was 95 to 98% or more after 1 day, 75 to 88% after 5 days, and 60 to 85% after 10 days. Thus, sodium citrate had a very favorable effect.

(3) At the storage temperature of 70° C., residual kallikrein activity in the absence of sodium citrate was about 70% after 2 hours, about 60% after 4 hours, and 50% after 6 hours. In the presence of sodium citrate, residual activity was 80 to 85% after 2 hours, 70–78% after 4 hours, and 70–75% after 6 hours, indicating that sodium citrate showed its expected effect.

EXAMPLE 2

Materials (1) A 4.0% aqueous solution of potassium citrate ($K_3C_6H_5O_7 \cdot H_2O$, Wako Pure Chemical Industries, Ltd.) was prepared. As the osmotic pressure ratio of this solution was approximately 1.0, sodium chloride was not added. To 2.6 ml of an aqueous solution of human urine kallikrein (17.4 KU/ml) was added 12.4 ml of the above potassium citrate solution. This solution contained the same equivalent of citrate ion as the 3.0% solution of sodium citrate. This solution was distributed in 0.5 ml portions into 1-ml ampules which were then sealed to provide samples.

(2) The kallikrein solution without addition of a citric acid salt and the kallikrein solution containing 3% of sodium citrate were prepared in the same manner as Example 1.

The conditions of testing procedure and activity determination were the same as those used in the 70° C. storage test of Example 1. The results are shown in Table 5. The sample prepared by adding 3.3% of potassium citrate to an aqueous solution of kallikrein showed a remarkable heat stability as did the sample containing 3.0% of sodium citrate in comparison the kallikrein solution containing no citric acid salt.

TABLE 5

|   | Hour 0 | Hour 2 | Hour 4 | Hour 6 |
| --- | --- | --- | --- | --- |
| Control (no citric acid salt) | 624.10 | 457.47 | 385.34 | 296.63 |
|   |        | 73.30% | 61.90% | 47.53% |
| 3% Sodium citrate | 586.11 | 505.99 | 448.65 | 419.54 |
|   |        | 86.33% | 76.55% | 71.58% |
| 3.3% Potassium citrate | 603.25 | 514.08 | 465.93 | 427.06 |
|   |        | 85.22% | 77.24% | 70.79% |

(Note)
Kallikrein activities in the examples were measured as follows. The kallikrein unit was determined by the vasodilator assay of the human urine kallikrein extracted and purified from human urine by the present inventors (Journal of Biochemistry 58, 201, 1965) and the assay method determinations were made by the fluorescent using Pro—Phe—Arg—MCA (Journal of Biochemistry 82, 1495, 1977) using the above purified sample as a standard.

EXAMPLE 3

In accordance with Example 1, sodium citrate was added in a concentration of 0.1 to 1.0% to the solution of human urine kallikrein for testing the heat stability and the variation per day of the kallikrein in the solution.

1. Materials

To aqueous solutions of human urine kallikrein (90 KU/ml), sidium citrate was added in a concentration of 0.1%, 0.25%, 0.5% and 1.0%, followed by adjusting the osmotic pressure ratio of the solution to 1.0 with sodium chloride. Each of these solution was distributed in 0.5 ml portions into 1 ml-ampules which were then sealed to provide samples.

2. Test method

Temperature conditions were settled to at room temperature, 50° C. and 60° C. and hour conditions to for 0 to 90 days.

The kallikrein activity before the test was taken as 100% and the residual activity rate was determined after each settled days.

3. Determination

The determination of kallikrein activity was carried out by MCA substrate hydrolytic activity, samely as in Example 1.

4. Results

Test for heat stability and variation per day with the solutions of human urine kallikrein gave results as shown in Tables 6 to 8.

The above-mentioned Tables lead to the following conclusions:

(1) Under the storage conditions of room temperature for 90 days, residual kallikrein activity in the absence of sodium citrate is 92.4% after 30 days, 91.1% after 60 days and 92.3% after 90 days, showing considerable stability. While, when 0.1 to 1.0% of sodium citrate was added, residual kallikrein activities were averaged 93.6% after 90 days, showing almost no effect by the addition of the stabilizer at room temperature.

(2) At the storage conditions of 50° C. for 90 days, residual kallikrein activity in the absence of sodium citrate decreased to 98.9% after 30 days, 83.9% after 60 days and 78.0% after 90 days. Whereas, in the presence of 0.1 to 1.0% of sidium citrate, residual kallikrein activity was not less than 98.5% after 30 days, not less than 93.8% after 60 days and 93.5 to 99.2% after 90 days, showing clearly the effect of sodium citrate.

(3) At the storage conditions of 60° C. for 60 days, residual kallikrein activity in the absence of sodium citrate was 76% after 7 days, 42% after 14 days, 39% after 30 days and 2.78% after 60 days, which indicates that the residual activity decreased day by day to almost no activity after 60 days. Whereas, in the presence of 0.1 to 1.0% of sodium citrate, residual activity was almost 100% after 14 days and 65 to 77% even after 30 days.

As mentioned abvoe, no significant difference was observed at room temperature for 90 days between the absence and presence of 0.1 to 1.0% of sodium citrate in the solution of human urine kallikrein, however, in accelerated tests at 50° C. and 60° C., the presence of sodium citrate in the solution clearly shows its stabilizing effect.

TABLE 6

Heat Stability of Human Urine Kallikrein (room temperature, 90 days)

| Level of addition of sodium citrate (%) | Day 0 | Day 30 | Day 60 | Day 90 |
|---|---|---|---|---|
| 0 | *608.45 | 562.01 | 554.27 | 561.58 |
|   |   | **92.4% | 91.1% | 92.3% |
| 0.1 | 655.75 | 608.45 | 621.78 | 602.43 |
|   |   | 92.8% | 94.8% | 91.9% |
| 0.25 | 626.94 | 594.69 | 615.33 | 594.26 |
|   |   | 94.9% | 98.1% | 94.8% |
| 0.5 | 648.87 | 641.99 | 611.89 | 586.09 |
|   |   | 98.9% | 94.3% | 90.3% |
| 1.0 | 621.78 | 655.75 | 608.45 | 628.66 |
|   |   | 105.5% | 97.9% | 101.1% |

*n mols aminomethylcoumarine/min./ml(sample)
**Residual activity, with the activity on 0 day being taken as 100% (the same applies hereinafter)

TABLE 7

Heat-stability of human urine kallikrein (50° C., 90 days)

| Level of addition of sodium citrate (%) | Day 0 | Day 7 | Day 14 | Day 30 | Day 60 | Day 90 |
|---|---|---|---|---|---|---|
| 0 | *608.45 | 581.36 | 635.11 | 601.57 | 510.41 | 474.72 |
|   |   | **95.5% | 104.4% | 98.9% | 83.9% | 78.0% |
| 0.1 | 655.75 | 675.96 | 654.89 | 709.93 | 615.33 | 628.66 |
|   |   | 103.1% | 99.9% | 108.3% | 93.8% | 95.9% |
| 0.25 | 626.94 | 641.99 | 688.00 | 652.31 | 594.69 | 586.09 |
|   |   | 102.4% | 109.7% | 104.0% | 94.9% | 93.5% |
| 0.5 | 648.87 | 641.99 | 674.67 | 641.99 | 611.89 | 616.62 |
|   |   | 98.9% | 104.0% | 98.9% | 94.3% | 95.0% |
| 1.0 | 621.78 | 703.05 | 686.28 | 628.66 | 615.33 | 616.62 |
|   |   | 113.1% | 110.4% | 101.1% | 99.0% | 99.2% |

TABLE 8

Heat-stability of human urine kallikrein (60° C., 60 days)

| Level of addition of sodium citrate (%) | Day 0 | Day 7 | Day 14 | Day 30 | Day 60 |
|---|---|---|---|---|---|
| 0 | *608.45 | 466.55 | 256.71 | 236.50 | 16.77 |
|   |   | **76.7% | 42.2% | 38.9% | 2.78% |
| 0.1 | 655.75 | 635.54 | 655.75 | 425.70 | 111.37 |
|   |   | 96.9% | 100% | 64.9% | 17.0% |
| 0.25 | 626.94 | 588.24 | 688.43 | 449.78 | 249.41 |
|   |   | 93.8% | 109.8% | 71.7% | 33.4% |
| 0.5 | 648.87 | 696.17 | 688.43 | 466.55 | 270.47 |
|   |   | 107.3% | 106.1% | 71.9% | 41.7% |
| 1.0 | 621.78 | 628.66 | 648.44 | 478.59 | 327.66 |
|   |   | 101.1% | 104.3% | 77.0% | 52.7% |

We claim:

1. A process for preparing a heat-stable aqueous solution of human urine kallikrein, which comprises contacting an effective amount of a pharmaceutically acceptable citric acid salt with human urine kallikrein in the form of aqueous solution.

2. A process according to claim 1 wherein the citric acid salt is dissolved in the solution in a concentration of about 1 to 5 percent.

3. A process according to claim 1 wherein the citric acid salt is sodium citrate or potassium citrate.

4. In the process of preparing a heat-stable aqueous solution of human urine kallikrein, the step which comprises dissolving human urine kallikrein and sodium or potassium citrate in a concentration of about 1 to 5 percent into water.

5. In a process for preparing a solution of human urine kallikrein, the steps which comprise dissolving human urine kallikrein and sodium or potassium citrate in a concentration of 1 to 5 percent into water, and heating the resulted aqueous solution to a temperature of 60° to 70° C., thereby the solution is sterilized without inactivating a substantial amount of the kallikrein.

6. A process for inactivating microorganisms and/or viruses possibly existing in the aqueous solution of human urine kallikrein which comprises heating human urine kallikrein with 1 to 5 percent of sodium or potassium citrate in an aqueous solution to a temperature of 60° to 70° C.

7. A heat-stable human urine kallikrein composition comprising an aqueous solution of human urine kallikrein and a stabilizing effective amount of a pharmaceutically acceptable salt of citric acid.

8. A composition according to claim 7 wherein the citric acid salt is present in a concentration of about 1 to 5%.

9. A composition according to claim 7 wherein the citric acid salt is sodium citrate or potassium citrate.

* * * * *